(12) United States Patent
Graves

(10) Patent No.: US 6,365,904 B1
(45) Date of Patent: Apr. 2, 2002

(54) SYSTEM AND METHOD OF HEAT SIGNATURE VERIFICATION/AUTHENTICATION OF AN OBJECT

(75) Inventor: Todd L. Graves, Garland, UT (US)

(73) Assignee: Iomega Corporation, Roy, UT (US)

( * ) Notice: Subject to any disclaimer, the term of this patent is extended or adjusted under 35 U.S.C. 154(b) by 0 days.

(21) Appl. No.: 09/533,154

(22) Filed: Mar. 23, 2000

(51) Int. Cl.⁷ .............................. F21V 9/16; G01J 1/58
(52) U.S. Cl. .................... 250/458.1; 250/459.1
(58) Field of Search ............... 250/458.1, 459.1

(56) References Cited

U.S. PATENT DOCUMENTS

| | | | |
|---|---|---|---|
| 5,949,539 A | 9/1999 | Britton, Jr. et al. | 356/317 |
| 5,986,272 A | 11/1999 | Britton, Jr. et al. | 250/459.1 |
| 6,181,662 B1 * | 1/2001 | Krieger et al. | 369/70 |
| 6,264,107 B1 * | 4/2001 | Thomas, III et al. | 235/468 |
| 6,266,211 B1 * | 7/2001 | Thomas, III et al. | 360/133 |

* cited by examiner

*Primary Examiner*—Ricky Mack
(74) *Attorney, Agent, or Firm*—Woodcock Washburn LLP

(57) ABSTRACT

The validity or authenticity of a latent illuminance material is established by heating or cooling the material to a predetermined temperature and then determining its decay time constant at that temperature. If the decay time constant is substantially equal to a predetermined value it is determined that the material is authentic. Thus, the authenticity of a material is determined by temporarily changing its decay time constant by way of temporarily changing the material's temperature using a heater or refrigerator. A light source illuminates the marker and the marker emits illuminance as phosphorescence. A photosensor detects the emitted illuminance, and the decay time constant is determined.

21 Claims, 10 Drawing Sheets

SYSTEM AND METHOD OF HEAT SIGNATURE VERIFICATION/AUTHENTICATION OF AN OBJECT

FIELD OF THE INVENTION

The present invention relates in general to methods and apparatus for verifying or authenticating an object that emits light. More particularly, the present invention relates to verifying or authenticating an object by determining its decay time constant at a predetermined temperature.

BACKGROUND OF THE INVENTION

Disk drives for receiving removable disk cartridges, including conventional 3.5 inch floppy disk drives, must have some mechanism for detecting the insertion or presence of a disk cartridge in the drive. The actuator that carries the recording heads of the disk drive across the recording surfaces of the disk should not be allowed to move unless the presence of an appropriate disk cartridge which is non-drive damaging is detected. The removability feature requires that the disk drive have a cartridge insertion opening into which foreign objects can be inserted. If these objects physically engage the drive as a legitimate cartridge would, then the heads could be loaded onto or into the foreign object, thereby destroying the drive. Also, the spindle motor of the disk drive will be activated by a falsely detected foreign object, thereby generating particle debris. In the prior art, mechanical switches are typically employed to detect the presence of a disk cartridge within the drive. Such switches are typically positioned such that when a disk cartridge is inserted fully into the drive, the cartridge contacts the switch, thereby providing an indication that the disk cartridge is present.

The ability to discriminate between cartridge types after insertion into a data storage drive but prior to putting the read/write heads on the recording media is of significant value and utility. Principally this utility comes from the ability to detect the difference between various capacities or generations of data storage cartridges in a downward media compatible data storage drive. This discrimination capability allows for drive/media specific adjustments to be made such as media rotation rate, data channel rates, location of Z track for initial seeking, or even mechanical adjustment in the drive such as the active engagement of new crash stop locations. The ability of a disk drive to predetermine the type/generation of data storage cartridge inserted into it prior to enabling the spin-up and engagement of read/write elements also provides the drive system designer with new possibilities for cross-platform interchangeability.

Recently, in various industries such as the distribution industry, phosphors have been used in the control of goods by means of bar codes, and furthermore, bar codes are printed on various prepaid cards and passing cards, and these bar codes are read by optical reading apparatuses, such as scanners, to perform the desired actions. Moreover, various attempts have been made to apply forgery prevention means to credit cards and prepaid cards or to detect forged cards. For example, the marks such as bar codes are printed with an ink containing a phosphor by offset printing or by using an ink ribbon to form latent image marks. The latent image marks are irradiated with a semiconductor laser beam to excite the phosphor and the light emitted from the phosphor is received to read the bar code information by an optical reading apparatus. These techniques use the content or spectral shift from the irradiating light source for identification.

Pending U.S. patent application Ser. No. 09/161,007, filed on Sep. 25, 1998, which is a continuation-in-part application of U.S. patent application Ser. No. 08/936,970, filed on Sep. 26, 1997, both of which are incorporated herein by reference, describes a latent illuminance marker and systems and methods for using the decay time constant of the marker to identify, verify or authenticate the object that the marker is attached to. A latent illuminance marker having a particular decay time constant is attached to an object to be verified. Light is illuminated on the marker, and then turned off. The decay time constant of the material in the marker is measured and compared to a predetermined value. If the measured decay time constant equals the predetermined value, then it is determined that the object is identified, verified, or authenticated.

However, some latent illuminance markers can exhibit the predetermined decay time constant at the standard operating temperature (e.g., at room temperature, during normal use, in a disk drive) but do not have the desired characteristics (material properties) of a true or authentic marker, such as the desired decay time constant, at non-operating temperatures. In other words, non-authentic markers can exhibit the correct decay time constant at the standard operating temperature, although they do not have the other characteristics of an authentic marker. Thus, these markers cannot be trusted to be authentic markers or markers having the true desired characteristics, which could lead to reliability problems, for example, such as the misidentification of the object to which the marker is, or will be, attached.

SUMMARY OF THE INVENTION

The present invention is directed to systems and methods for identifying a type of material in a marker having a temperature, comprising: a temperature altering device for setting the temperature of the material to a predetermined temperature; a light source for emitting light to illuminate the marker; a photodetector for measuring an intensity of light received from the marker; and a microprocessor for determining a decay time constant of the material responsive to the intensity and for determining the type of material responsive to the decay time constant at the predetermined temperature.

According to further aspects of the present invention, a comparator compares the decay time constant to a predetermined decay time constant to produce a comparison result wherein the microprocessor determines the type of material responsive to the comparison result.

Another embodiment within the scope of this invention includes systems and methods for verifying the authenticity of an object having a marker disposed thereon, the marker comprising a latent illuminance material, comprising: a temperature altering device for setting the temperature of the latent illuminance marker to a predetermined temperature; a light source for emitting light to illuminate the marker; a photodetector for measuring an intensity of light received from the marker; and a microprocessor for determining a decay time constant of the latent illuminance material responsive to the intensity of the light and for verifying the authenticity of the object responsive to the decay time constant at the predetermined temperature.

The foregoing and other aspects of the present invention will become apparent from the following detailed description of the invention when considered in conjunction with the accompanying drawings.

DESCRIPTION OF EXEMPLARY EMBODIMENTS AND BEST MODE

Figure 1:
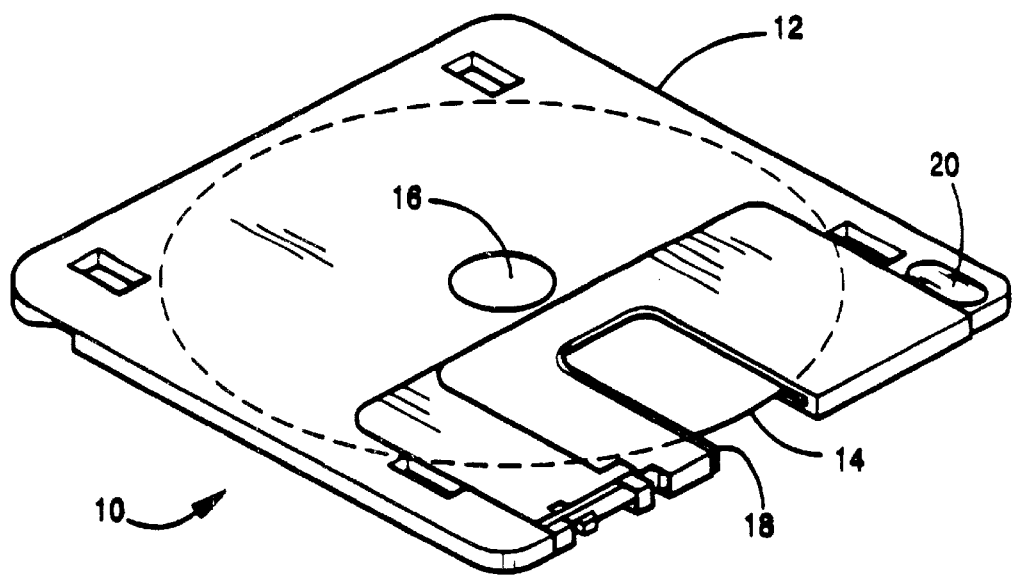
FIG. 1 shows an exemplary data storage cartridge for use with the present invention.

As described above, a latent illuminance marker (hereinafter also referred to as a tag) can be used to identify and discriminate the type of data storage cartridge (hereinafter also referred to as a disk cartridge) that has been inserted into a disk drive. The present invention provides a system and method for determining the authenticity of the marker so that it can be ascertained with near certainty that an inserted object into a disk drive is an appropriate disk cartridge. The present invention can also be used to determine the authenticity of the marker for identifying or verifying any object that the marker is attached to. The tag system is a highly effective discriminant of appropriate cartridge insertion for a disk drive and can also be used to prevent unauthorized copies of software from being easily reproduced and used in disk drives. It should be noted that the term "illuminance" as used herein includes, but is not limited to, irradiance and the spectrum of light including ultra-violet (UV), visible, and near infrared.

FIGS. 1 and 2A–2C show an exemplary cartridge and devices to which the present invention is applicable. The exemplary cartridge and associated disk drive are described in U.S. Pat. No. 5,809,520, issued Sep. 15, 1998, to Edwards et al., which is incorporated herein by reference, although any disk cartridge and drive can be used.

The disk cartridge 10 comprises an outer casing 12 and a disk-shaped recording medium 14 which is affixed to a disk hub 16 that is rotatably mounted in the casing 12. An opening on the bottom shell of the casing 12 provides access to the disk hub 16. A head access opening in the front peripheral edge 18 of the disk cartridge 10 provides access to the recording surfaces of the disk by the recording heads of a disk drive.

In accordance with the present invention, a latent illuminance marker, or tag, 20 is positioned on the disk cartridge 10 to be detected by a detector in a disk drive, or other marker verification apparatus.

Figure 2A:
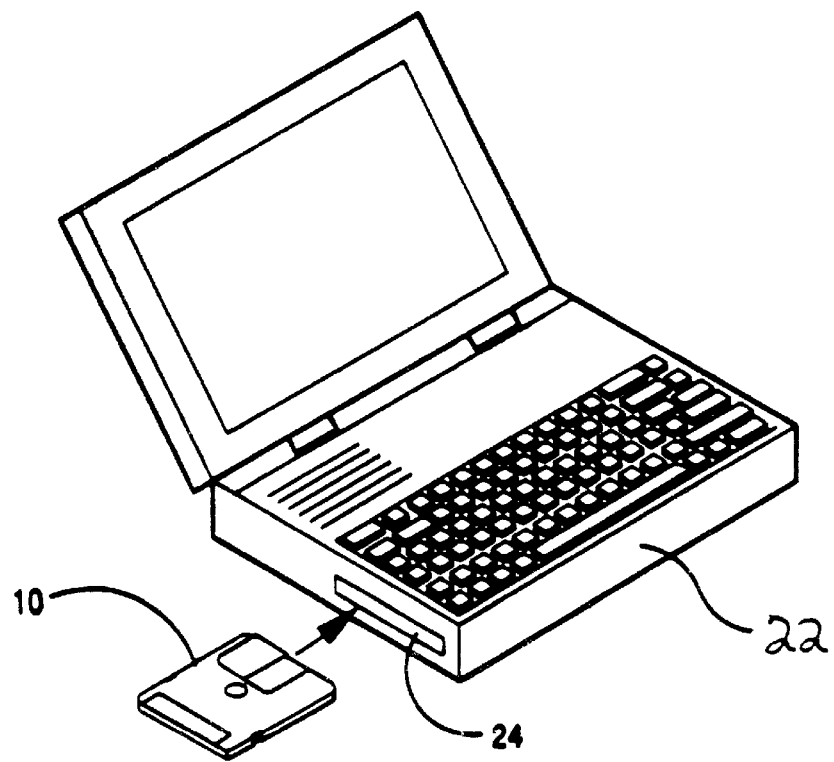
FIG. 2A is a perspective view of an exemplary device in which a data storage cartridge according to the present invention can be used.
Figure 2B:
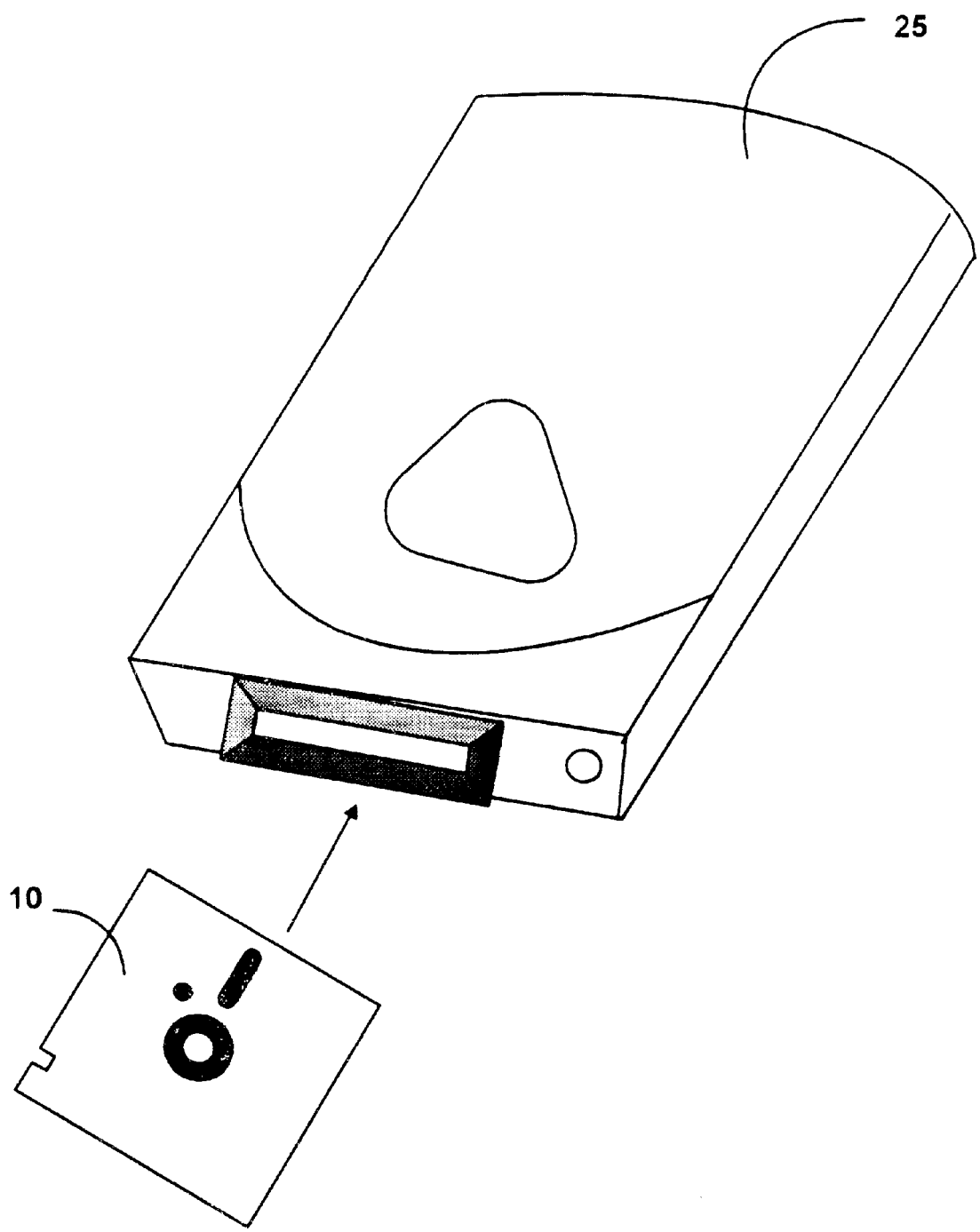
FIG. 2B is a perspective view of another exemplary device in which a data storage cartridge according to the present invention can be used.
Figure 2C:
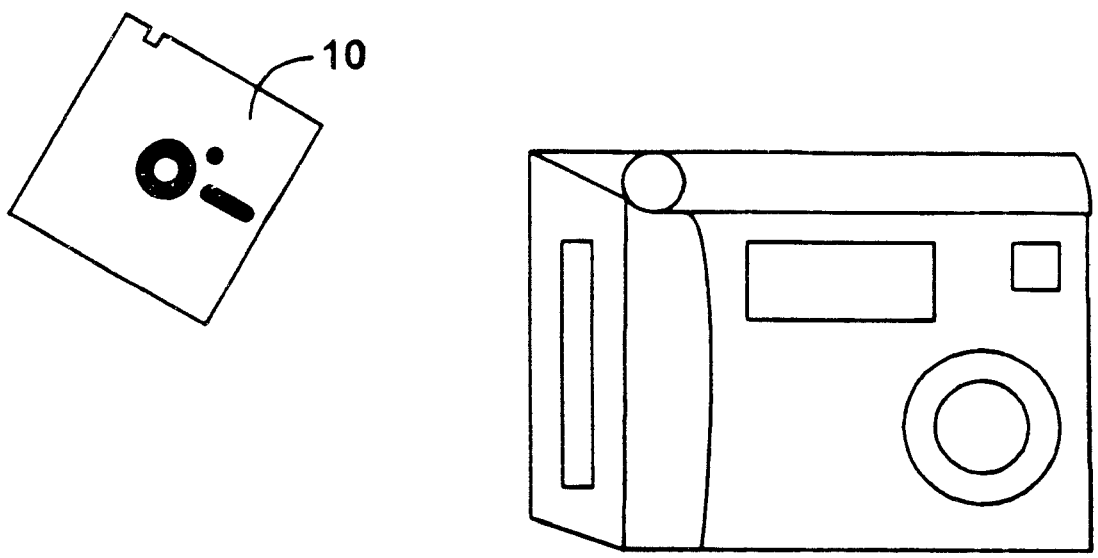
FIG. 2C is a perspective view of another exemplary device in which a data storage cartridge according to the present invention can be used.

FIG. 2A shows a laptop computer 22 which has a disk drive 24 for receiving the disk cartridge 10 of FIG. 1. The drive 24 may be the Iomega ZIP™ drive which is disclosed and claimed in the U.S. patents identified in U.S. Pat. No. 5,638,228. The drive 24 can either be incorporated into a computer or another data generating device such as a digital camera, smart phone, or personal digital assistant or can be a standalone portable drive, separable from a data generating device such as a computer, a digital camera, a smart phone, or personal digital assistant, for example. FIG. 2B shows a portable data storage drive or disk drive 25 for receiving the disk cartridge 10 of FIG. 1, and FIG. 2C shows a digital camera 26 for receiving the disk cartridge 10 of FIG. 1.

A latent illuminance tag, preferably phosphorescent, can be attached to a data storage cartridge as a sticker, or printed into, or applied via suspension in an adhesive compound such as a UV curable epoxy onto, a data storage cartridge. On each disk cartridge having an authorized copy of the software, there is a tag which is preferably coated with a phosphorescent photoluminant material which serves to identify the type or generation of disk cartridge and distinguish it from other types of disk cartridges and purely passive light reflectors.

Figure 3A:
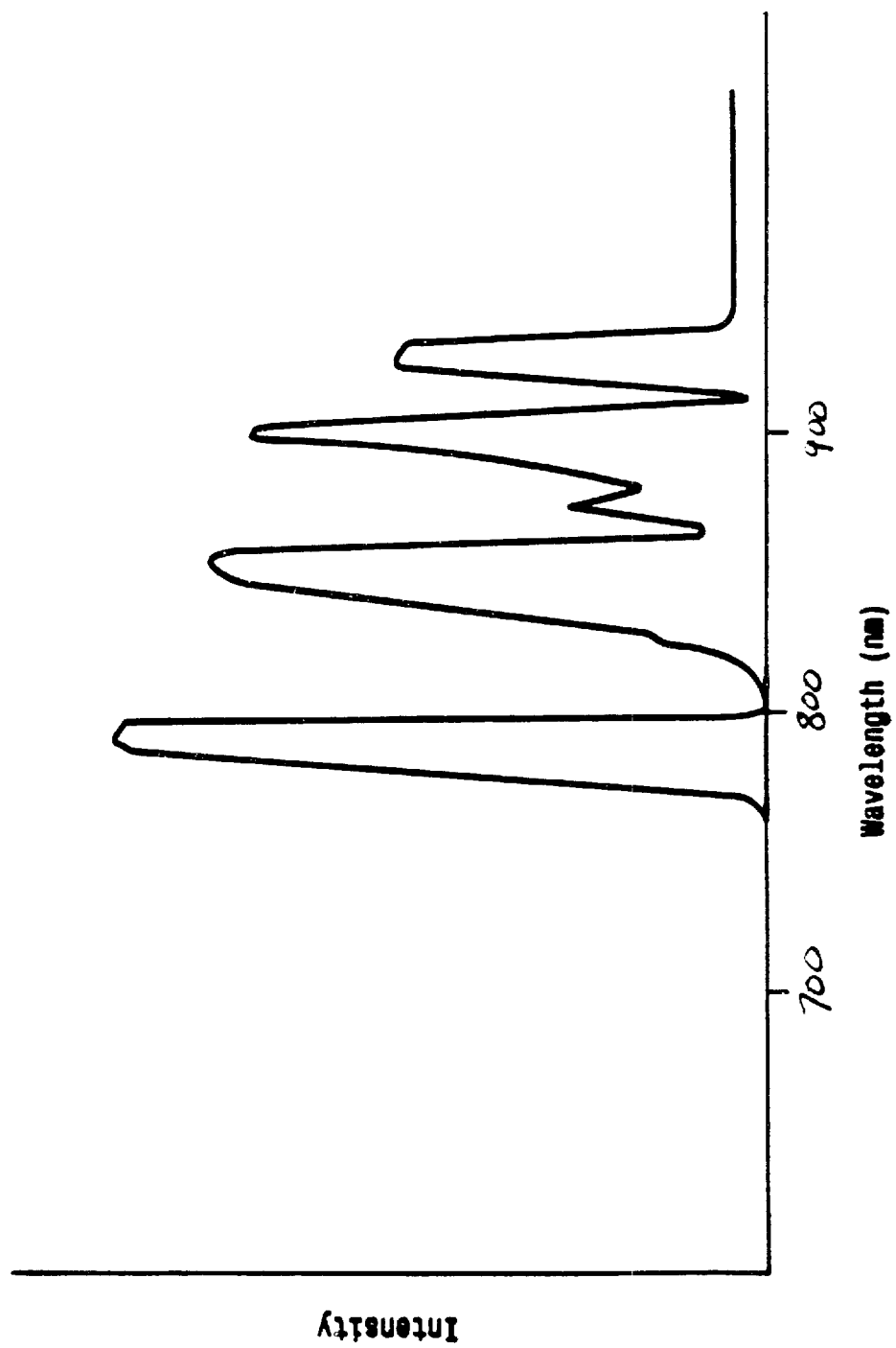
FIG. 3A is an exemplary latent illuminance output spectrum for a tag in accordance with the present invention.

The phosphor type materials used in the phosphorescent tag fluoresce for a period of time after a light source, preferably an LED, that has illuminated the tag is turned off. The LED strikes the tag at an excitation wavelength and the light emitted from the tag has a wavelength (or wavelengths) that is shifted from the excitation wavelength. The wavelength(s) can be shorter or longer than the excitation wavelength. As described above, the light emission from the tag is called phosphorescence. An exemplary latent illuminance output spectrum for a tag in accordance with the present invention is shown in FIG. 3A. The output spectrum is characteristic of the material that comprises the tag. The intensity of the illuminance (light) emitted at at least one of the wavelengths (e.g., about 780 nm) can be monitored to measure a decay time constant, as described below.

Preferably, the latent illuminance material is excited with light close to a single wavelength (e.g., about 660 nm). The latent irradiance emitted by the latent illuminance material can be at a single wavelength, or at a spectrum of wavelengths (e.g., between about 780 and about 900 nm). In the latter case, the signal used to determine the decay period (hereinafter also referred to as a decay time) is measured as the aggregate of the spectrum of wavelengths being detected by the sensor. The decay time can then be used to determine the decay time constant.

Although any material exhibiting latent illuminant properties or characteristics can be used in accordance with the present invention, a phosphorescent material is used in a preferred embodiment of this invention. Any material or combination of materials exhibiting latent illuminance properties or characteristics can be used as the latent illuminance material in accordance with the present invention, including any phosphor or combination or blend of phosphors. Preferred phosphors include rare-earth phosphors including oxides, oxysulfides, silicates, and alumites as well as other photoluminant materials and compounds. There are many combinational possibilities for photoluminant materials.

The tag will emit illuminance (light) in accordance with the output spectrum for a period of time after being illuminated with a light source. The decay time for the emitted illuminance ranges from sub-microseconds to several minutes, and preferably between about 50 $\mu$sec and about 3,000 $\mu$sec, depending on the material that is phosphorescing and the wavelengths that are being monitored. A decay time used to specify the tag is the time it takes for the latent irradiance to decay to some fraction or percentage, such as 37%, of its initial value. The decay time constant is determined based on the decay time. Any method of determining decay time and decay time constant can be used, and a preferred method is described in pending U.S. patent application Ser. No. 09/161,007, filed on Sep. 25, 1998, which is a continuation-in-part application of U.S. patent application Ser. No. 08/936,970, filed on Sep. 26, 1997, both of which are incorporated herein by reference.

Figure 3B:
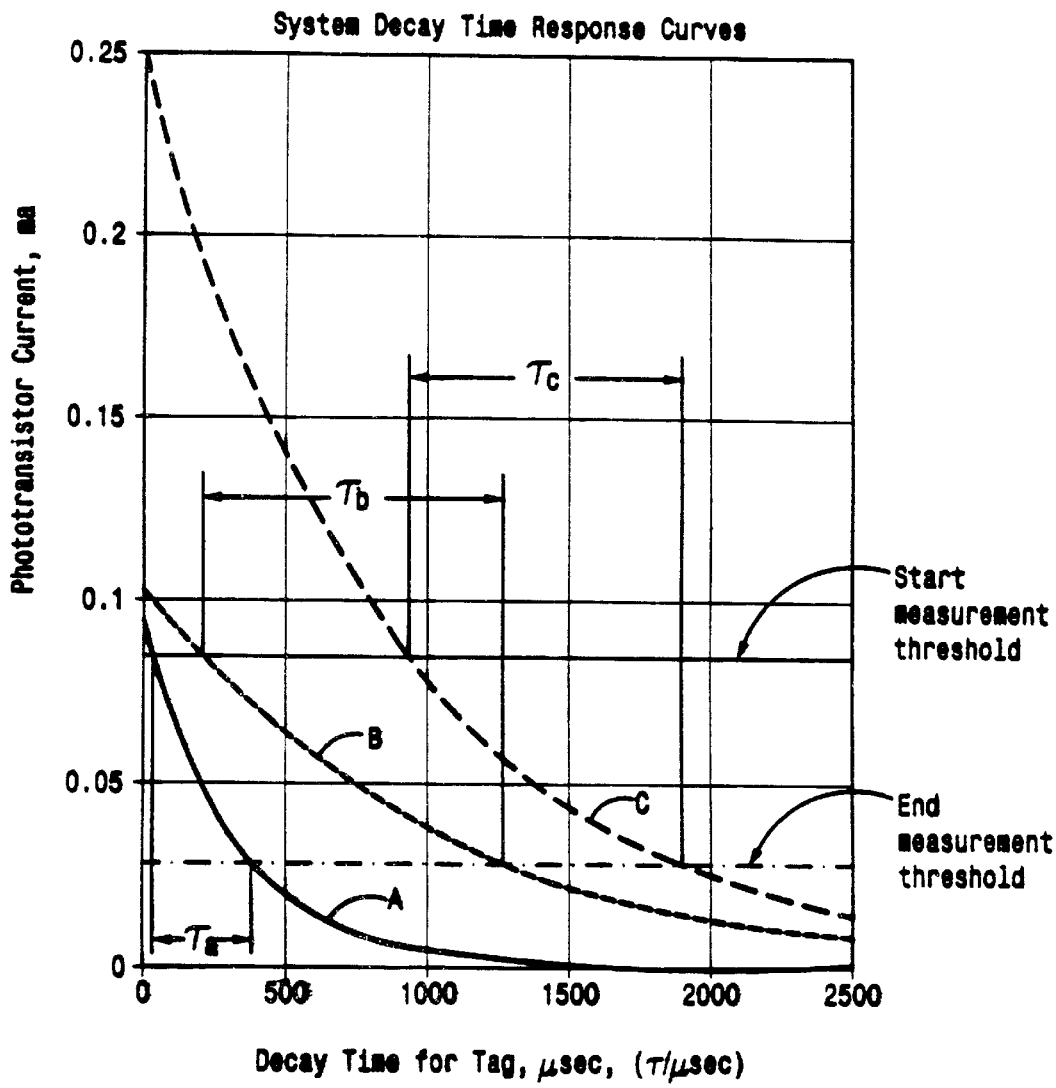
FIG. 3B is a diagram of exemplary decay rates for exemplary tag materials in accordance with the invention.

In accordance with a preferred embodiment, the decay in irradiance takes the form $e^{-t/(T/X)}$ where T is the decay time constant for a predetermined amount of decay, X is a predetermined constant that preferably ranges between about 0.36 and about 2.3, and t is elapsed time from when the charging LED is turned off, or the elapsed time for the decaying signal level to pass from a first predetermined magnitude or intensity level through a second lower level which is fixed and predetermined, and is preferably a predetermined percentage below the first magnitude level, but can be a predetermined percentage below the initial value. For example, for a decay of about 30% of the initial latent illuminance, X is about 0.36. FIG. 3B illustrates this decay for three different exemplary tag materials, A, B, and C, as a graph of phototransistor current versus decay time for the tag. As described below, a phototransistor or photodiode are the preferred detectors used to detect the emitted illuminance from a tag.

Figure 3C:
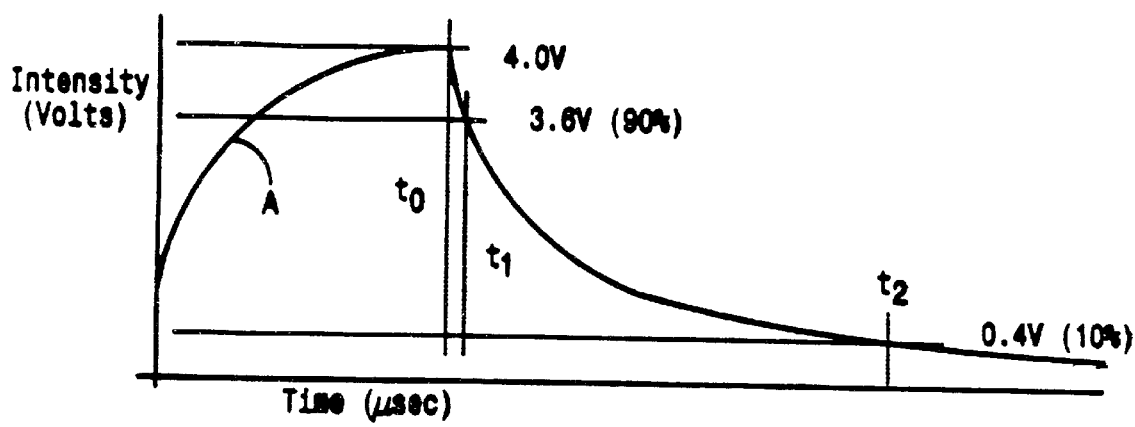
FIG. 3C is an exemplary decay pattern for a tag in accordance with the present invention.

FIG. 3C shows an exemplary decay pattern for a tag in accordance with the present invention. The intensity is measured for a predetermined wavelength. As the tag is being illuminated (charged) by the LED light source, it begins to emit illuminance, as indicated by line A. The LED light source is turned off at time $t_o$, and the tag thereafter emits latent illuminance from an initial peak value, such as about 4.0 volts, to a low value, ultimately approaching about 0 volts. The decay time is measured between two or more thresholds, such as between 90% and 10% of the initial value; i.e., the time between about 3.6 volts and 0.4 volts, or $t_2-t_1$. This decay from the initial 3.6 volt threshold level to a 0.4 volt threshold level illustrates an embodiment where about an 89% decay time is measured (100*(3.6–0.4)/3.6). A decay time constant is determined based on the decay time. The determined decay time constant is compared with a predetermined decay time constant to determine whether or not the data storage cartridge or disk that has been inserted in the disk drive is appropriate for use with the disk drive. If so, the read/write heads of the disk drive are then able to engage the disk without risk of damage. Moreover, the data storage cartridge can be identified as a particular type or generation, and the disk drive can engage it accordingly. Although the preferred embodiment is directed to an exponential decaying latent illuminance material, it is also appreciated that non-exponential optically decaying latent illuminance materials can also be used with the present invention.

Figure 4:
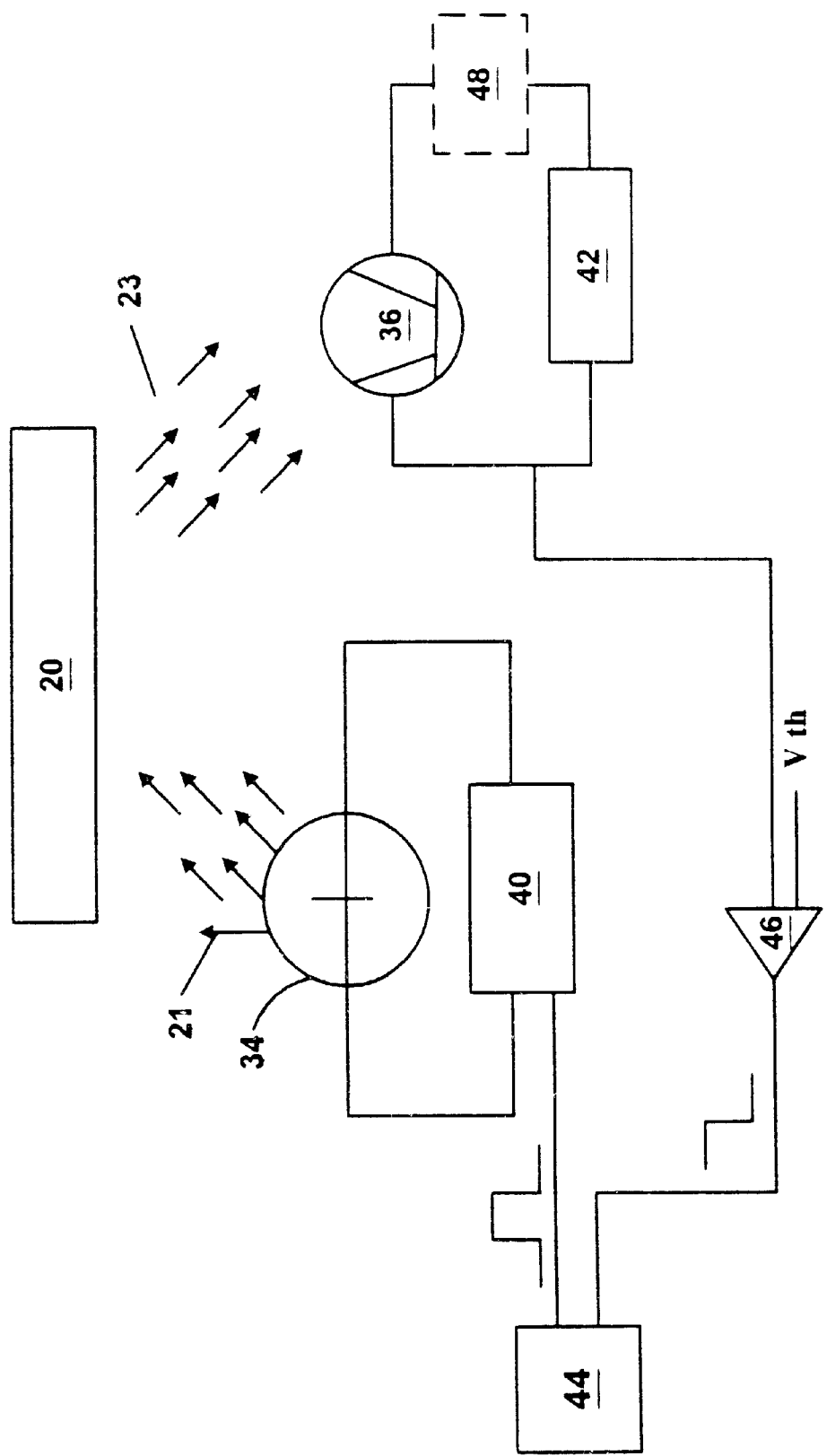
FIG. 4 shows a block diagram of an exemplary system used for determining the decay time constant in accordance with the present invention.

FIG. 4 shows a block diagram of an exemplary system used for determining decay time and decay time constant in accordance with the present invention. A light source 34, preferably an LED, illuminates a latent illuminance tag 20 with light 21 and is then turned off. The tag 20 can either be standalone (e.g., not affixed to an object to be identified), as shown, or can be attached to an object to be identified, such as the data storage cartridge shown in FIG. 1. The LED 34 is driven by LED switching and current limiting electronics 40, and a microprocessor 44 that sends pulse commands to the electronics 40. The tag 20 emits illuminance 23, having an initial intensity value at a particular wavelength or wavelengths, which is detected by a detector 36, preferably a phototransistor or photodiode. Preferably, the detector 36 waits a predetermined time, such as about 10 $\mu$sec, after the LED is turned off before beginning measurement of the latent illuminance 23 at the particular wavelength(s) from the tag. Gain, preferably 100×, is applied to the output of the phototransistor or photodiode 36 by a gain stage 42. The output of the gain stage 42 is provided to a comparator 46 which compares the emitted illuminance with a threshold Vth. The results of the comparison are provided to the microprocessor 44 which measures the timing, determines the decay rate or time and decay time constant, and identifies the object (e.g., a disk cartridge) for validation, as described above. Element 48 contains optional filters.

More particularly, when a data storage cartridge is inserted into a disk drive, the light source 34, preferably an LED, emits a short intense pulse of light 21. The light 21 can be one pulse or a continuous cycle of pulses. LEDs are capable of handling large current surges for short periods to generate bright flashes of light. The outputted LED light 21 illuminates the latent illuminance tag 20 and thereby excites atoms or ions which emit light 23 as they decay to lower energy levels. The phosphor type materials used in the preferred latent illuminance tag 20 fluoresce for a period of time after the LED 34 is turned off. The photonic sensor 36 is in close proximity to the LED 34. This sensor 36 is initially saturated by the emitted light from the tag 20, preferably significantly above the high detection threshold level such that component life and manufacturing tolerances are accommodated (i.e., do not significantly affect the performance of the device). Once the LED 34 is turned off, the disk drive microprocessor 44 or a functionally similar system monitors the output of the photonic sensor 36 and, in an exemplary embodiment, determines the decay time and the decay time constant. The decay time constant determined by the drive microprocessor 44 provides information by which the drive can determine which generation or type of cartridge has been inserted, for example.

The thresholds are preferably fixed, predetermined values, but it is understood that the microprocessor could measure the initial intensity value of the latent illuminance and, based on the initial value, determine the thresholds. Moreover, the thresholds could be fixed intensity values (e.g., about 3.0 volts and about 1.0 volts) determined independently, and not determined responsive to a percentage of the initial value or any other threshold.

Figure 5:
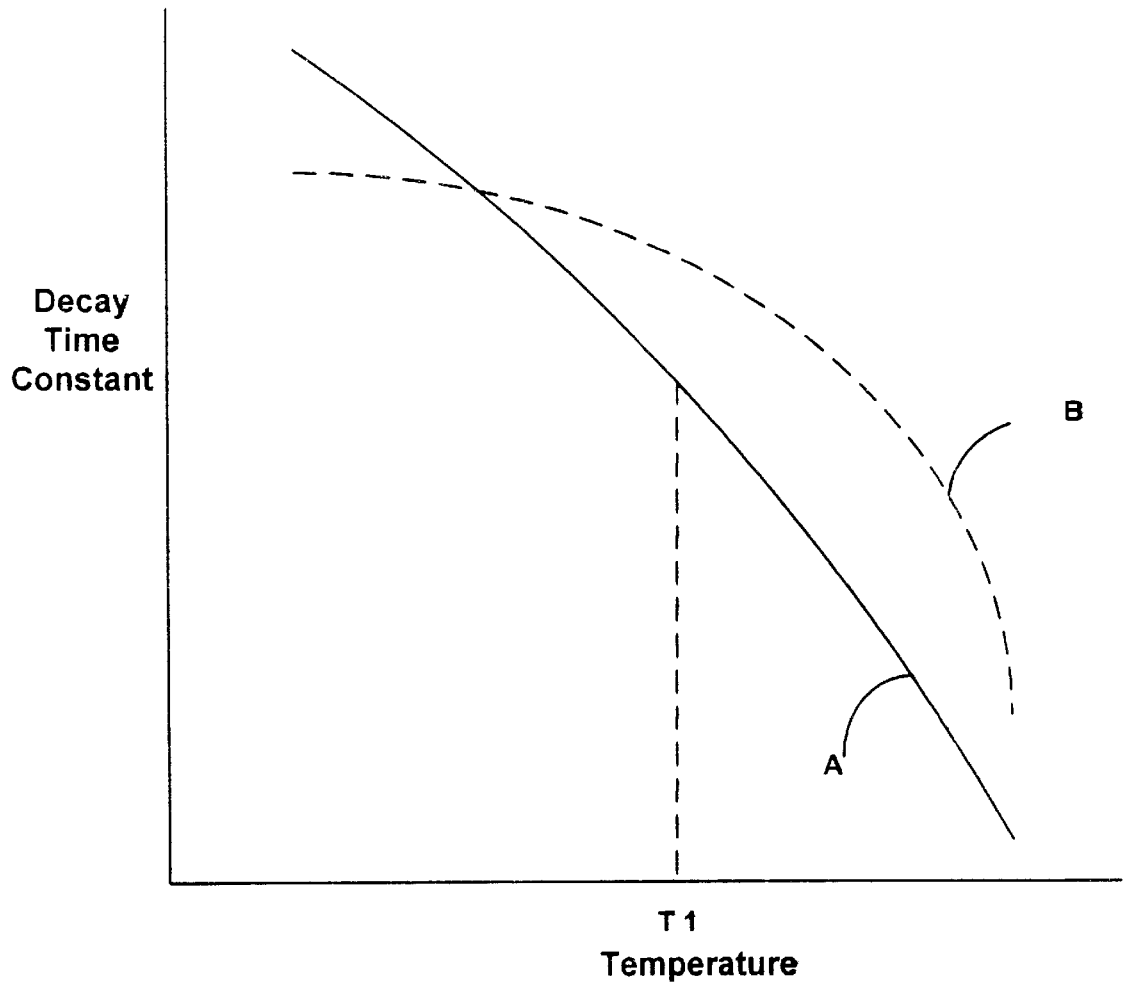
FIG. 5 shows an exemplary diagram of the decay time constant of a latent illuminance material as a function of temperature.

The decay time constant of a material varies with temperature. An exemplary diagram of the decay time constant of a latent illuminance material as a function of temperature for two different latent illuminance materials A and B is shown in FIG. 5. Note that the two materials exhibit the same decay time constant at one temperature Ti and have different decay time constants at another temperature. Thus, different materials could have the different time constant vs. temperature diagrams, yet still have the same decay time constant at a particular temperature (e.g., the standard operating temperature). Accordingly, it is desirable to determine the decay time constant of materials at a temperature other than the standard operating temperature (i.e., an increased or decreased temperature) to ensure that the materials are substantially identical.

Assuming that a material exhibits a predetermined decay time constant at room temperature, the validity or authenticity of the material in the tag (and hence, the object the tag is, or will be, attached to) may be established by heating or cooling the tag (and thus the latent illuminance material therein) to a predetermined temperature and then determining its decay time constant at that temperature. The new decay time constant must be substantially equal to a predetermined value or it is determined that the material is not authentic. Thus, the present invention is directed to verifying the authenticity of a material by temporarily changing its decay time constant by way of temporarily changing the material's temperature.

The testing is performed using an oven or a freezer or other temperature altering apparatus or system and an optical response measurement system such as the one described with respect to FIG. 4. A hand held device having a temperature controlled heating element and a light-free optical test chamber can also be used.

Figure 6:
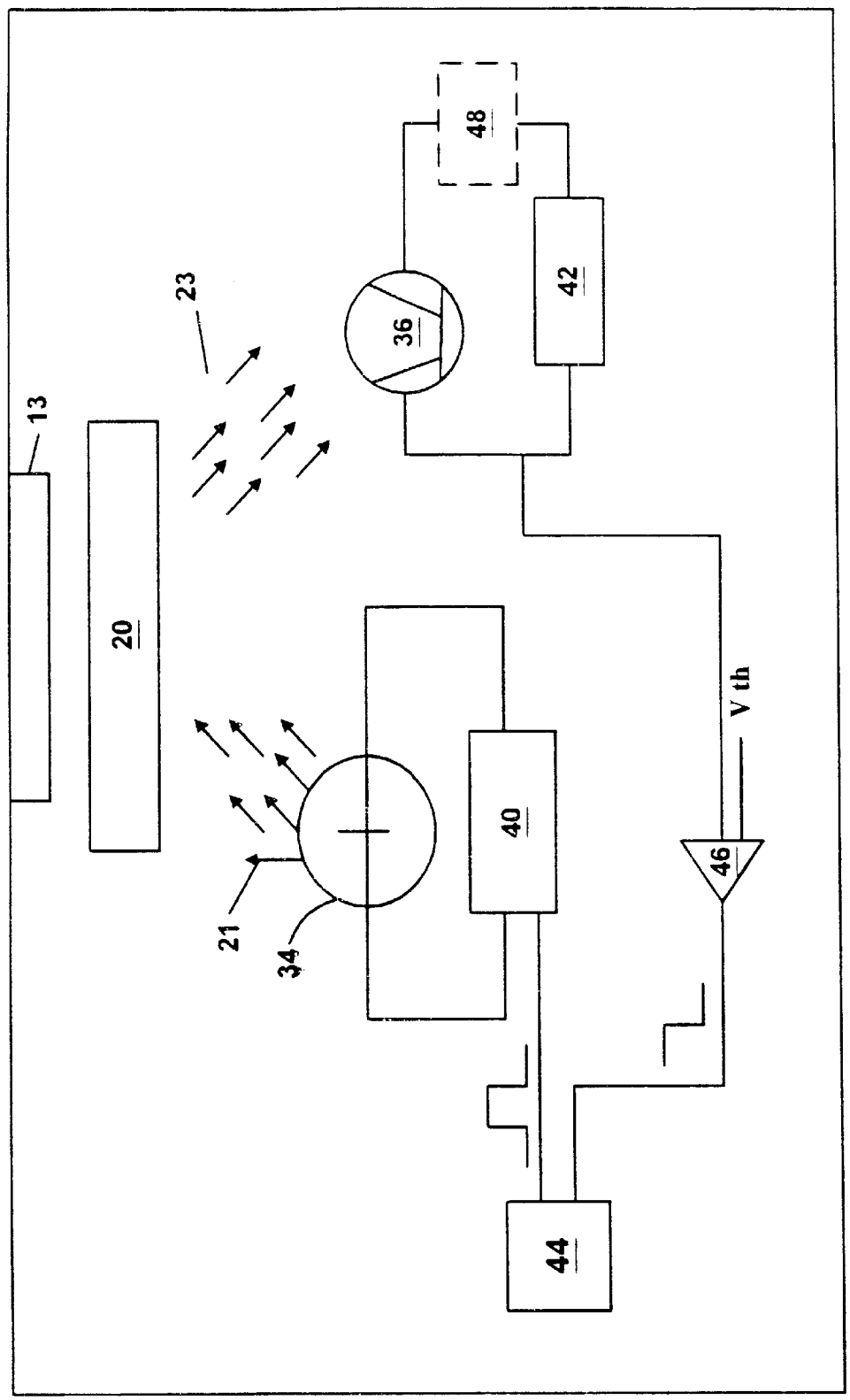
FIG. 6 shows a block diagram of an exemplary system comprising a temperature modifying device, such as a heater or a refrigerator, and a decay time constant determining system in accordance with the present invention.

After the temperature of the tag is changed by heating or cooling, for example, the decay time constant is determined, as described above with respect to FIG. 4. Preferably, the system of FIG. 4 is incorporated into the oven or freezer so that the decay time constant can be determined immediately after the material in the tag is heated or cooled to the desired temperature. In this manner, there is a reduced likelihood that the temperature of the material and the tag will substantially change either prior to or during the measurement at the raised or lowered temperature. FIG. 6 shows a block diagram of an exemplary system comprising a temperature altering device 13, such as a heater or a refrigerator, and a decay time constant determining system in accordance with the present invention. The temperature altering device 13 alters the temperature of the marker 20 prior to the determination of the tag's decay time constant.

Figure 7:
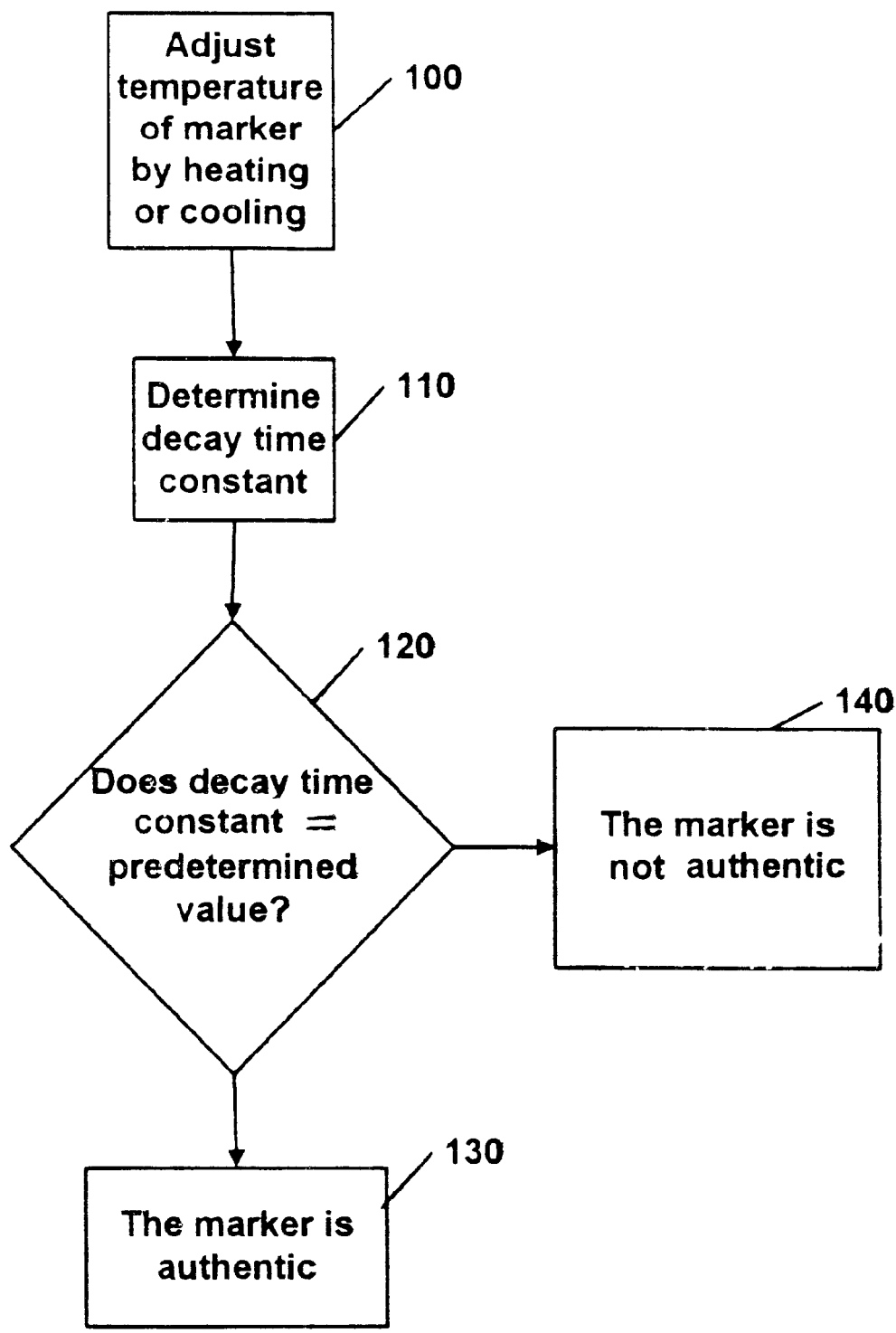
FIG. 7 is a flow chart of an exemplary method in accordance with the present invention.

FIG. 7 is a flow chart of an exemplary method in accordance with the present invention. Initially, the material, or tag comprising the material, is placed in a chamber comprising a temperature altering device, such as a heater or a refrigerator. At step 100, the temperature is adjusted until the temperature of the material reaches the desired predetermined temperature. Preferably, the predetermined temperature is different from the temperature of the environment in which the tag will be typically subsequently operating. At step 10, the decay time constant is determined using any method, including the methods described above. At step 120, the decay time constant is compared to a predetermined number corresponding to the authentic material. If the decay time constants are substantially similar, then it is determined that the material being tested is authentic at step 130; otherwise, then it is determined that the material is not authentic at step 140. Moreover, additional decay time constants can be determined at different temperatures for even further authentication and verification accuracy.

Although the present invention has been described herein with respect to cartridge detection, it can be used in any object detection or discrimination apparatus or application, such as cartridgeless disks (e.g., optical disks) and anti-counterfeiting apparatus and applications, and can be used to verify materials during any stage of the production process or product life cycle.

Although illustrated and described herein with reference to certain specific embodiments, the present invention is nevertheless not intended to be limited to the details shown. Rather, various modifications may be made in the details within the scope and range of equivalents of the claims and without departing from the invention.

What is claimed:

1. A system for identifying a type of material in a marker having a temperature, comprising:

a temperature altering device for setting the temperature of the material to a predetermined temperature;

a light source for emitting light to illuminate the marker;

a photodetector for measuring an intensity of light received from the marker; and a microprocessor for determining a decay time constant of the material responsive to the intensity and for determining the type of material responsive to the decay time constant at the predetermined temperature.

2. The system according to claim 1, further comprising a comparator for comparing the decay time constant to a predetermined decay time constant to produce a comparison result wherein the microprocessor determines the type of material responsive to the comparison result.

3. The system according to claim 1, wherein the temperature altering device is a heater.

4. The system according to claim 1, wherein the temperature altering device is a refrigerator.

5. The system according to claim 1, wherein the light source is a light emitting diode (LED) and the photodetector is one of a phototransistor and a photodiode.

6. The system according to claim 1, wherein the material comprises a latent illuminance material.

7. The system according to claim 6, wherein the latent illuminance material comprises a phosphor.

8. A method for identifying a type of material in a marker having a temperature, comprising:

setting the temperature of the material to a predetermined temperature;

emitting light to illuminate the marker;

measuring an intensity of light received from the marker;

determining a decay time constant of the material responsive to the intensity; and determining the type of material responsive to the decay time constant at the predetermined temperature.

9. The method according to claim 8, further comprising comparing the decay time constant to a predetermined decay time constant to produce a comparison result wherein the determining the type of material is responsive to the comparison result.

10. The method according to claim 8, wherein the temperature altering device is one of a heater and a refrigerator.

11. The method according to claim 8, wherein the light source is a light emitting diode (LED) and the photodetector is one of a phototransistor and a photodiode.

12. The method according to claim 8, wherein the material is a latent illuminance material.

13. The method according to claim 12, wherein latent illuminance material comprises a phosphor.

14. A system for verifying the authenticity of an object having a marker disposed thereon, the marker comprising a latent tilluminance material, comprising:

a temperature altering device for setting the temperature of the latent illuminance marker to a predetermined temperature;

a light source for emitting light to illuminate the marker;

a photodetector for measuring an intensity of light received from the marker; and a microprocessor for determining a decay time constant of the latent illuminance material responsive to the intensity of the light and for verifying the authenticity of the object responsive to the decay time constant at the epredetermined temperature.

15. The system according to claim 14, further comprising a comparator for comparing the decay time constant to a predetermined decay time constant to produce a comparison result wherein the microprocessor determines the authenticity of the object responsive to the comparison result.

16. The system according to claim 14, wherein the temperature altering device is one of a heater and a refrigerator.

17. The system according to claim 14, wherein the light source is a light emitting diode (LED) and the photodetector is one of a phototransistor and a photodiode.

18. A method for verifying the authenticity of an object having a marker disposed thereon, the marker comprising a latent illuminance material, comprising:

irradiating the marker with a source of irradiance;

detecting irradiance transmitted from the marker at a photodetector; and determining a decay time constant of the latent illuminance material responsive to the intensity of the light; and verifying the authenticity of the object responsive to the decay time constant at the predetermined temperature.

19. The method according to claim 18, further comprising comparing the decay time constant to a predetermined decay time constant to produce a comparison result wherein the verifying the authenticity of the object is responsive to the comparison result.

20. The method according to claim 18, wherein the temperature altering device is one of a heater and a refrigerator.

21. The method according to claim 18, wherein the light source is a light emitting diode (LED) and the photodetector is one of a phototransistor and a photodiode.

* * * * *